United States Patent [19]

Chang et al.

[11] Patent Number: 5,591,875
[45] Date of Patent: Jan. 7, 1997

[54] EPOXIDATION PROCESS

[76] Inventors: Te Chang, 839 Shaumont Dr.; David W. Leyshon, 408 Trio La., both of West Chester, Pa. 19382; Guy L. Crocco, 1514 Ridge Rd., Wilmington, Del. 19809

[21] Appl. No.: 587,183

[22] Filed: Jan. 16, 1996

Related U.S. Application Data

[63] Continuation of Ser. No. 510,221, Aug. 2, 1995, abandoned.

[51] Int. Cl.$^6$ ...................... C07D 301/12; C07D 303/04
[52] U.S. Cl. ............................................................. 549/531
[58] Field of Search ................................................ 549/531

[56] References Cited

U.S. PATENT DOCUMENTS

| | | | |
|---|---|---|---|
| 2,786,854 | 3/1957 | Smith et al. | 549/531 |
| 2,871,102 | 1/1959 | Rust et al. | 23/207 |
| 2,871,103 | 1/1959 | Skinner et al. | 23/207 |
| 3,156,709 | 11/1964 | Allan | 549/531 |
| 4,824,976 | 4/1989 | Clerici et al. | 549/531 |
| 4,833,260 | 5/1989 | Neri et al. | 549/531 |
| 4,859,785 | 8/1989 | Bellussi et al. | 549/531 |
| 4,937,216 | 6/1990 | Clerici et al. | 502/62 |
| 5,214,168 | 5/1993 | Zajacek et al. | 549/531 |
| 5,221,795 | 6/1993 | Clerici et al. | 549/531 |
| 5,252,758 | 10/1993 | Clerici et al. | 549/531 |
| 5,262,550 | 11/1993 | Crocco et al. | 549/531 |
| 5,374,747 | 12/1994 | Saxton et al. | 549/531 |
| 5,384,418 | 1/1995 | Zajacek et al. | 549/531 |
| 5,453,511 | 9/1995 | Saxton | 546/191 |

FOREIGN PATENT DOCUMENTS 6211821  8/1994  Japan .

OTHER PUBLICATIONS

Clerici et al., *J. Cat.* 129 pp. 159–167 (1991).
Clerici et al., *J. Cat.* 140 pp. 71–83 (1993).
*Applied Catalysis:General* 128 (1995) 89–96 "Oxidations Involving Phosphate Species Supported on TS–1:A novel class of gratted catalysts".

*Primary Examiner*—Joseph E. Evans

[57] ABSTRACT

In an epoxidation process wherein an olefin is reacted with hydrogen peroxide in the presence of a titanium-containing molecular sieve catalyst and a salt, the tendency of the catalyst to produce greater quantities of oxygen as it ages due to non-selective decomposition of the hydrogen peroxide may be counteracted by the addition of a chelating agent bearing hydroxyl, carboxyl, amino, and/or phosphoryl groups. The use of such a chelating agent enables selectivity to epoxide to be maintained at a desirably high level for a prolonged period of time in a continuous epoxidation unit.

22 Claims, No Drawings

EPOXIDATION PROCESS

This is a continuation of application Ser. No. 08/510,221, filed Aug. 2, 1995, now abandoned.

FIELD OF THE INVENTION

This invention relates to methods whereby the efficiency of an olefin epoxidation reaction may be enhanced. In particular, the invention pertains to an epoxidation process wherein a chelating agent is utilized to suppress the non-selective decomposition of hydrogen peroxide to oxygen.

BACKGROUND OF THE INVENTION

It is well known that the epoxidation of olefinic compounds with hydrogen peroxide may be effectively catalyzed by certain synthetic zeolites containing titanium atoms (see, for example, U.S. Pat. No. 4,833,260). While selectivity to the desired epoxide is generally high, U.S. Pat. No. 4,824,976 proposes that the non-selective ring-opening reactions which take place when epoxidation is performed in a protic medium such as water or alcohol may be suppressed by treating the catalyst prior to the reaction or during the reaction with a suitable acid neutralizing agent. The neutralizing agent is said to neutralize acid groups on the catalyst surface which tend to promote by-product formation. Neutralization, according to the patent, may be accomplished with water soluble basic substances chosen from among strong bases such as NaOH and KOH and weak bases such as $NH_4OH$, $Na_2CO_3$, $NaHCO_3$, $Na_2HPO$, and analogous potassium and lithium salts including $K_2CO_3$, $Li_2CO_3$, $KHCO_3$, $LiHCO_3$, and $K_2HPO_4$, alkali and/or alkaline earth salts of carboxylic acids having from 1 to 10 carbon atoms and alkali and/or alkaline earth alcoholates having from 1 to 10 carbon atoms.

Co-pending U.S. application Ser. No. 08/396,319, filed Feb. 28, 1995, discloses that by carrying out a titanium silicalite-catalyzed epoxidation in the presence of low concentrations of a non-basic salt (i.e., a neutral or acidic salt) selectivity to epoxide may unexpectedly be significantly improved by reducing the quantity of ring-opened by-products formed.

We have now found that while epoxide ring-opening may be effectively suppressed by performing the epoxidation in the presence of a suitable source of ammonium, alkali metal, or alkaline earth metal cations, whether basic, neutral, or acidic in character, non-selective hydrogen peroxide decomposition to oxygen and water tends to gradually increase as the titanium silicalite catalyst ages. For example, when titanium silicalite is used in a continuous fixed bed system to epoxidize propylene in the presence of a cation source such as ammonium hydroxide, selectivity to the desired propylene oxide product decreases over time while selectivity to oxygen increases to the range of about 8 to 15%. The mechanism responsible for this loss in epoxide selectivity is not well understood. It would be highly desirable, however, to find a means of alleviating the effects of aging on catalyst performance such that epoxide ring-opening and hydrogen peroxide decomposition are simultaneously suppressed in order to maximize the yield of epoxide obtained over the life of a particular catalyst charge.

SUMMARY OF THE INVENTION

We have now unexpectedly discovered that the tendency of a titanium-containing molecular sieve catalyst to gradually deteriorate in performance (as measured by non-selective hydrogen peroxide decomposition to oxygen) when used in an olefin epoxidation reaction together with a source of cations may be ameliorated by performing the epoxidation in the presence of a chelating agent such as a compound having two or more groups selected from the group consisting of amino, hydroxyl, carboxyl, phosphoryl and combinations thereof. In one embodiment of the invention, the chelating agent is employed in anionic (deprotonated) form with the salt generated functioning as a source of the ammonium, alkali metal, or alkaline earth metal cation.

The present invention thus provides a method for epoxidizing an olefin comprising reacting said olefin with hydrogen peroxide in a liquid phase within a reaction zone in the presence of a titanium-containing molecular sieve catalyst, a salt comprising an anionic species and a cation selected from the group consisting of ammonium cations, alkali metal cations, and alkaline earth metal cations and an amount of a chelating agent effective to reduce non-selective decomposition of the hydrogen peroxide to molecular oxygen upon aging of the catalyst.

DETAILED DESCRIPTION OF THE INVENTION

The hydrogen peroxide ($H_2O_2$) utilized as the oxidant in the present invention may be obtained from any suitable source, including, for example, from autoxidation of secondary alcohols using air or other source of molecular oxygen. Suitable secondary alcohols include both aliphatic alcohols such as isopropanol and cyclohexanol as well as aromatic alcohols such as alpha methyl benzyl alcohol and anthrahydroquinones (including alkyl-substituted anthrahydroquinones). The crude reaction product thereby generated may be either used directly in the epoxidation process of this invention or, if so desired, purified, fractionated, concentrated, ion exchanged, or otherwise processed prior to such use. For example, the ketone generated as an autoxidation co-product may be separated, in whole or in part, from the hydrogen peroxide by distillation (where the ketone is relatively volatile) or by extraction with water (where the ketone is substantially immiscible with or insoluble in water). The hydrogen peroxide may alternatively be generated in situ by, for example, combining oxygen, secondary alcohol, olefin, titanium-containing molecular sieve catalyst, chelating agent and salt within a reaction zone under conditions effective to accomplish simultaneous secondary alcohol autoxidation and olefin epoxidation. Generally speaking, it will be desirable to employ initial hydrogen peroxide concentrations of from about 0.5 to 20 weight percent in the liquid phase within the reaction zone.

The ethylenically unsaturated substrate epoxidized in the process of this invention is preferably an organic compound having from two to ten carbon atoms and at least one ethylenically unsaturated functional group (i.e., a carbon-carbon double bond) and may be a cyclic, branched or straight chain aliphatic olefin. More than one carbon-carbon double bond may be present in the olefin; dienes, trienes, and other polyunsaturated substrates thus may be used.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, the trimers and tetramers of propylene, cyclopentene, cyclohexene, cycloheptene, cyclooctene, cyciooctadiene, dicyclopentadiene, methylenecyclopropane, methylenecyclopentane, methylenecyclohexane, vinylcyclohexane, and vinyl cyclohexene.

Mixtures of olefins may be epoxidized and resulting mixture of epoxides either employed in mixed form or separated into the different component epoxides.

The process of this invention is especially useful for the epoxidation of $C_2$–$C_{10}$ olefins having the general structure

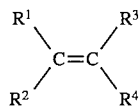

wherein $R^1$, $R^2$, $R^3$, and $R^4$ are the same or different and are selected from the group consisting of hydrogen and $C_1$–$C_8$ alkyl (selected so that the total number of carbons in the olefin does not exceed 10).

The process of this invention is also suitable for use in epoxidizing olefins containing functional groups other than aliphatic hydrocarbyl moieties. For example, the carbon-carbon double bond can be substituted with groups such as —$CO_2H$, —$CO_2R$, —CN, or —OR wherein R is an alkyl, cycloalkyl, aryl or aralkyl substituent. The radicals $R^4$, $R^2$, $R^3$, and $R^4$ in the structural formula shown hereinabove may contain aryl, aralkyl, halo, nitro, sulfonic, cyano, carbonyl (e.g., ketone, aldehyde), hydroxyl, carboxyl (e.g., ester, acid) or ether groups. Examples of olefins of these types include allyl alcohol, styrene, allyl chloride, allyl methyl ether, allyl phenyl ether, methyl methacrylate, acrylic acid, methyl acrylate, stilbene, and the like.

The amount of hydrogen peroxide relative to the amount of olefin is not critical, but most suitably the molar ratio of olefin: hydrogen peroxide is from about 100:1 to 1:10 when the olefin contains one ethylenically unsaturated group. The molar ratio of ethylenically unsaturated groups in the olefin to hydrogen peroxide is more preferably in the range of from 1:2 to 10:1.

The titanium-containing molecular sieves useful as catalysts in the epoxidation step of the process comprise the class of zeolitic substances wherein titanium is substituted for a portion of the silicon atoms in the lattice framework of a molecular sieve. Such substances are well-known in the art.

Particularly preferred catalysts include the classes of molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta. The titanium catalyst preferably contains no non-oxygen elements other than titanium and silica in the lattice framework, although minor amounts of boron, iron, aluminum, and the like may be present.

Titanium-containing molecular sieve catalysts suitable for use in the process of this invention will generally have a composition corresponding to the following empirical formula $xTiO_2$: $(1-x)SiO_2$, where x is between 0.0001 and 0.500. More preferably, the value of x is from 0.01 to 0.125. The molar ratio of Si:Ti in the lattice framework of the molecular sieve is advantageously from 9.5:1 to 99:1 (most preferably, from 9.5:1 to 60:1 ). The use of relatively titanium-rich catalysts may also be desirable.

The amount of catalyst employed is not critical, but should be sufficient so as to substantially accomplish the desired epoxidation reaction in a practicably short period of time. The optimum quantity of catalyst will depend upon a number of factors including reaction temperature, olefin reactivity and concentration, hydrogen peroxide concentration, type and concentration of organic solvent as well as catalyst activity and the type of reactor or reaction system (i.e., batch vs. continuous) employed. In a batch-type or slurry reaction, for example, the amount of catalyst will typically be from 0.001 to 10 grams per mole of olefin. In a fixed or packed bed system, the optimum quantity of catalyst will be influenced by the flow rate of reactants through the fixed bed; typically, from about 0.05 to 2.0 kilograms hydrogen peroxide per kilogram catalyst per hour will be utilized. The concentration of titanium in the liquid phase reaction mixture will generally be from about 10 to 10,000 ppm.

The catalyst may be utilized in powder, pellet, microspheric, extruded, monolithic or any other suitable physical form. The use of a binder (co-gel) or support in combination with the titanium-containing molecular sieve may be advantageous. Supported or bound catalysts may be prepared by the methods known in the art to be effective for zeolite catalysts in general. Preferably, the binder or support is essentially non-acidic and does not catalyze the non-selective decomposition of hydrogen peroxide or ring-opening of the epoxide.

Illustrative binders and supports include titania, silica, alumina, silica-alumina, silica-titania, silica-thoria, silica-magnesia, silica-zironia, silica-beryllia, and ternary compositions of silica with other refractory oxides. Also useful are clays such as montmorillonites, koalins, bentonites, halloysites, dickites, nacrites, and ananxites. The proportion of molecular sieve to binder or support may range from 99:1 to 1:99, but preferably is from 5:95 to 80:20.

A critical feature of the process of this invention is the presence of a salt. While the precise mechanism by which the improvements of the process are realized is not known, it is believed that the salt interacts in a favorable way with the titanium-containing molecular sieve catalyst so as to suppress undesired side reactions such as epoxide ring-opening and solvent oxidation. In one embodiment, the catalyst is pretreated (i.e., prior to epoxidation) with the salt. One suitable pretreatment method involves forming a slurry of the catalyst in a diluted solution of the salt in a suitable solvent for the salt such as water and/or alcohol and stirring the slurry at a temperature of from 20° C. to 100° C. for a time effective to incorporate sufficient salt into the pores of the molecular sieve. The catalyst is thereafter separated from the slurry by suitable means such as filtration, centrifugation, or decantation, washed if so desired, and then, optionally, dried of residual solvent. In another pretreatment method, an as-synthesized catalyst is impregnated with a solution of the salt and then calcined. In a preferred embodiment, however, the salt is introduced into the reaction zone separately from the catalyst during epoxidation. For example, the salt may be suitably dissolved in the hydrogen peroxide feed, which typically will also contain a solvent such as water, alcohol, and/or ketone. In a continuous process, the concentration of salt in the feed entering the reaction zone may be periodically adjusted as desired or necessary in order to optimize the epoxidation results attained. It may, for example, be advantageous to use a constant salt concentration, to introduce the salt at intermittent intervals, or to increase or decrease the salt concentration over time.

A salt is a compound formed when the proton of an acid is replaced by a metal cation or its equivalent (e.g., $NH_4^+$). Suitable salts for the purpose of this invention include those substances which comprise an anion and a cation wherein the cation is preferably selected from ammonium ($NH_4$), alkali metals (especially Li, Na, K), and alkaline earth metals. The salt may be acidic, neutral, or basic in character. Preferred anions include, but are not limited to, halide (especially Cl and Br), nitrate ($NO_3$), and sulfate ($SO_4$). Other anions such as carboxylates (e.g., formate, acetate), carbonates (e.g., carbonate, bicarbonate), hydroxide, alkoxides, and the like may also be used. Exemplary nonbasic salts suitable for use include lithium chloride, lithium bromide, sodium chloride, sodium bromide, lithium nitrate, sodium nitrate, potassium nitrate, lithium sulfate, sodium sulfate, potassium sulfate, lithium, magnesium, calcium, barium, and ammonium acetate (and other nonbasic salts of carboxylic acids, especially $C_1$–$C_{10}$ carboxylic acids), ammonium dihydrogen phosphate, sodium dihydrogen phosphate, potassium dihydrogen phosphate, and disodium dihydrogen pyrophosphate. Exemplary basic salts include, but are not limited to, sodium hydroxide, potassium hydroxide, ammonium hydroxide, sodium carbonate, sodium bicarbonate, dibasic sodium phosphate, tribasic sodium phosphate, and the analogous potassium and lithium salts. Mixtures or combinations of salts may be advantageously employed. Preferably, the salt is soluble in the liquid phase of the epoxidation reaction mixture (which typically is comprised of hydrogen peroxide, solvent, and olefin).

The process of this invention also requires a chelating agent containing a plurality of donor atoms (e.g., O, N, S) that can combine by coordinate bonding with a single metal atom to form a cyclic structure called a chelation complex (chelate). The chelating agent may be organic or inorganic in character and preferably has at least two oxygen-containing functional groups per molecule, wherein said functional groups are desirably selected from the group consisting of hydroxyl, carboxyl, phosphoryl, or combinations thereof. The chelating agent thus may be bidentate, tridentate, tetradentate, or otherwise multidentate in character. The functional groups may be present in protonated or deprotonated form. For example, "carboxyl" includes

as well as

groups, "hydroxyl" includes —OH as well as —O$^\ominus$ groups, and "phosphoryl" includes

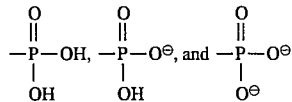

groups. Preferably, at least one carboxyl group or phosphoryl group is present. The functional groups are advantageously situated in the chelating agent such that the atoms capable of coordinating to a single metal ion are separated by between 3 and 7 atoms; said intervening atoms may be phosphorus, carbon, and the like. Nitrogen-containing functional groups, such as tertiary amine groups, capable of coordinating with metal ions may also be present in the chelating agent.

Specific illustrative polyfunctional chelating agents include polyphosphonic acids (e.g., aminotrimethylene phosphonic acid, ethylenediamine tetramethylene phosphonic acid, hydroxyethylidenediphosphonic acid), polyphosphoric acids ($H_{n+z}P_nO_{3n+1}$, wherein n>1, including pyrophosphoric acid, triphosphoric acid, and metaphosphoric acid as well as organophosphoric acids such as phytic acid), hydroxycarboxylic acids (e.g., malic acid, gluconic acid, hydroxyethylethylenediamine triacetic acid, N,N-bis(2-hydroxyethyl)glycine, tartaric acid, citric acid), aminocarboxylic acids (e.g., ethylenediamine tetraacetic acid, ethylenediamine-di-o-hydroxy phenyl acetic acid, 1,2-diamino cyclohexane tetracetic acid, nitrilotriacetic acid), polyamines (e.g., triethylene tetramine, triaminotriethylamine, ethylenediamine), polycarboxylic acids (e.g., diglycolic acid) aminoalcohols (e.g., triethanol amine), as well as alkali metal, alkaline earth metal, and ammonium salts thereof.

When the chelating agent is utilized in deprotonated form, it may advantageously function simultaneously as the anionic species in the salt. That is, the salt may be an alkali metal, alkaline earth metal, or ammonium salt of a chelating agent as herein defined. Such a species may be introduced directly into the reaction zone or, alternatively, formed in situ by the combination of the chelating agent in protonated form and a base such as an alkali metal or ammonium hydroxide. The chelating agent in such an embodiment may be fully or partially deprotonated.

To avoid an undesirable decrease in the rate of hydrogen peroxide conversion, the concentration of salt in the liquid phase within the reaction zone should generally be no greater than 0.02M. Below 0.00001M, little or no enhancement in epoxide selectivity is generally observed. The optimum concentration of salt will vary depending upon a number of factors, including, for example, the chemical identity of the salt, temperature, solvent, space velocity, and the like, but may be readily determined by routine experimentation. Generally speaking, the level of salt in the liquid phase epoxidation reaction mixture is desirably maintained from about 1 to 1000 ppm.

The amount of chelating agent present within the liquid phase the reaction zone is selected so as to effectively reduce the non-selective decomposition of the hydrogen peroxide to molecular oxygen upon aging of the titanium-containing molecular sieve catalyst as compared to the level of $O_2$ generation which would result in the absence of the chelating agent. The optimum amount of the chelating agent will vary depending upon parameters such as the chemical identities of the salt and the agent selected for use as well as the epoxidation conditions, but may be readily determined by routine experimentation. Typically, the chelating agent is utilized at a concentration of from about 1 to 1000 ppm in the liquid phase of the reaction mixture.

The epoxidation reaction temperature is preferably from 0° C. to 100° C. (more preferably from 20° C. to 80° C.), which has been found to be sufficient to accomplish selective conversion of the olefin to epoxide within a reasonably short period of time with minimal non-selective decomposition of the hydrogen peroxide. It is generally advantageous to carry out the reaction to achieve as high a hydrogen peroxide conversion as possible, preferably at least 50%, more preferably at least 90%, most preferably at least 99%, consistent with reasonable selectivities. The optimum reaction temperature will be influenced by catalyst concentration and activity, substrate reactivity, reactant concentrations, and type of solvent employed, among other factors. Reaction or residence times of from about 10 minutes to 48 hours will typically be appropriate, depending upon the above-identified variables. The reaction is preferably performed at atmospheric pressure or at elevated pressure (typically, between 1 and 100 atmospheres). Generally, it will be desirable to maintain the reaction components as a liquid mixture. For example, when an olefin such as propylene is used having a boiling point at atmospheric pressure which is less than the epoxidation temperature, a superatmospheric pressure sufficient to maintain the desired concentration of propylene in the liquid phase is preferably utilized.

The epoxidation process of this invention may be carried out in a batch, continuous, or semi-continuous manner using any appropriate type of reaction vessel or apparatus such as a fixed bed, transport bed, stirred slurry, or CSTR reactor. Known methods for conducting metal-catalyzed epoxidations using hydrogen peroxide will generally also be suitable for use. Thus, the reactants may be combined all at once or sequentially. For example, the hydrogen peroxide and/or the olefin may be added incrementally to the reaction zone.

Epoxidation may be performed in the presence of a suitable solvent in order to dissolve or disperse the reactants and to facilitate temperature control. Suitable solvents include, but are not limited to, water, alcohols (especially $C_1$–$C_{10}$ aliphatic alcohols such as methanol and isopropanol), ketones (especially $C_3$–$C_{10}$ ketones such as acetone), and mixtures of such solvents.

Once the epoxidation has been carried out to the desired degree of conversion, the epoxide product may be separated and recovered from the reaction mixture using any appropriate technique such as fractional distillation, extractive distillation, liquid-liquid extraction, crystallization, or the like. After separating from the epoxidation reaction mixture by any suitable method such as filtration (as when a slurry reactor is utilized, for example), the recovered titanium-containing molecular sieve catalyst may be economically re-used in subsequent epoxidations. Where the catalyst is deployed in the form of a fixed bed, the epoxidation product withdrawn as a stream from the epoxidation zone will be essentially catalyst free with the catalyst being retained within the epoxidation zone. Similarly, any unreacted olefin or hydrogen peroxide may be separated and recycled or otherwise disposed of. In certain embodiments of the instant process where the epoxide is produced on a continuous basis, it may be desirable to periodically or constantly regenerate all or a portion of the used catalyst in order to maintain optimum activity and selectivity. Suitable regeneration techniques are well-known and include, for example, calcination and solvent treatment. Regeneration can also include retreatment or reimpregnation with the salt.

From the foregoing description, one skilled in the art can readily ascertain the essential characteristics of this invention, and, without departing from the spirit and scope thereof, can make various changes and modifications of the invention to adapt it to various usages, conditions, and embodiments.

EXAMPLES

To demonstrate the benefits and advantages of the claimed process, a series of continuous propylene epoxidation runs was performed using a spinning basket CSTR wherein the catalyst comprised an extrudate containing 50% TS-1 titanium silicalite. The run conditions in each case were 140° F. (60° C.) 200 psig, and a weight hourly space velocity of 0.2 lb $H_2O_2$/lb./catalyst/hour. The base feed contained 2.5 weight % $H_2O_2$, 73 weight % isopropanol, 24 weight % water, 0.2 weight % methanol, 0.29 weight % acetic acid, and 0.1 weight % formic acid. To the base feed were added varying amounts of ammonium hydroxide and, in the runs illustrating the present invention "Dequest 2000" ATMP (aminotrimethylene phosphonic acid). The results obtained are listed in Table 1.

TABLE I

| Example No. | 1[3] | 2 | 3[3] | 4 | 5 | 6 |
|---|---|---|---|---|---|---|
| $NH_4OH$ in Feed, ppm | 78 | 78 | 234 | 234 | 234 | 234 |
| ATMP in Feed, ppm | 0 | 120 | 0 | 90 | 120 | 240 |
| Catalyst on Stream, hr | 350 | 455 | 230 | 630 | 510 | 590 |
| Propylene Oxide Selectivity[2], % | 77 | 77 | 84 | 86 | 85 | 85 |
| Oxygen Selectivity[2], % | 5.0 | 2.5 | 4.0 | 2.5 | 2.5 | 3.0 |
| $ROP^1$ Selectivity[2], % | 13 | 14 | 6 | 6 | 7 | 7 |
| $H_2O_2$ Conversion, % | 78 | 75 | 79 | 69 | 70 | 70 |

[1]ROP = propylene oxide ring-opening products = monopropylene glycol + propylene glycol isopropyl ether + the addition product of hydrogen peroxide and propylene oxide.
[2]based on hydrogen peroxide
[3]comparative example Comparative examples 1 and 3, wherein ammonium hydroxide but not ATMP was present in the epoxidation feed, indicate that while increasing the concentration of ammonium hydroxide decreases the quantity of undesired ring-opened products produced (as suggested by U.S. Pat. No. 4,824,976), the catalyst tends to generate relatively high levels of $O_2$ (from non-selective $H_2O_2$ decomposition) as it ages. Co-feeding 120 ppm ATMP chelating agent with the ammonium hydroxide in Example 2, however, significantly reduced the selectivity to $O_2$ even when the catalyst had been in use much longer than in Example 1 (455 hours v. 350 hours). Similarly, oxygen production was effectively suppressed under extended continuous reaction conditions in Examples 4–6 wherein the chelating agent was used together with ammonium hydroxide in the feed. Surprisingly, the chelating agent, although acidic in character, did not interfere with the beneficial effect of ammonium hydroxide (a basic substance) on propylene oxide side reactions.

We claim:

1. A method for epoxidizing an olefin comprising reacting said olefin with hydrogen peroxide in a liquid phase in a reaction zone in the presence of a titanium-containing molecular sieve catalyst, a salt comprising an anionic species and a cation selected from the group consisting of ammonium cations, alkali metal cations, and alkaline earth metal cations and an amount of a chelating agent effective to reduce non-selective decomposition of the hydrogen peroxide to molecular oxygen upon aging of the titanium-containing molecular sieve catalyst.

2. The method of claim 1 wherein the chelating agent has at least two functional groups per molecule, said functional groups being selected from the group consisting of amino, hydroxyl, carboxyl, phosphoryl, and combinations thereof.

3. The method of claim 1 wherein said salt is basic.

4. The method of claim 1 wherein said salt is neutral.

5. The method of claim 1 wherein said salt is acidic.

6. The method of claim 1 wherein the chelating agent is selected from the group consisting of polyphosphonic acids, polyphosphoric acids, hydroxycarboxylic acids, polycarboxylic acids, aminocarboxylic acids, polyamides, and alkali metal, alkaline earth metal, and ammonium salts thereof.

7. The method of claim 1 wherein the anionic species is selected from the group consisting of halides, phosphates, sulfates, carbonates, carboxylates, hydroxide, alkoxides, and nitrate.

8. The method of claim 1 wherein said reacting is performed at a temperature of from 1° C. to 100° C.

9. The method of claim 1 wherein said hydrogen peroxide is obtained by oxidation of isopropanol.

10. The method of claim 1 wherein the liquid phase is comprised of a solvent selected from the group consisting of water, $C_2$–$C_{10}$ alcohols, $C_3$–$C_{10}$ ketones, and mixtures thereof.

11. The method of claim 1 wherein the titanium-containing molecular sieve catalyst has an MFI, MEL, or zeolite beta topology.

12. The method of claim 1 wherein the olefin is a $C_2$–$C_{10}$ aliphatic olefin.

13. The method of claim 1 wherein the titanium-containing molecular sieve catalyst has a composition corresponding to the chemical formula $xTiO_2$:$(1-x)SiO_2$ wherein x is from 0.01 to 0.125.

14. The method of claim 1 wherein said reacting is carried out continuously.

15. The method of claim 1 wherein the titanium-containing molecular sieve catalyst is deployed in the reaction zone in the form of a fixed bed.

16. The method of claim 1 wherein the titanium-containing molecular sieve catalyst is deployed in the reaction zone in the form of a slurry in the liquid phase.

17. The method of claim 1 wherein the salt is present at a concentration of from 0.00001M to 0.02M in the liquid phase.

18. The method of claim 1 wherein the chelating agent is present at a concentration of from 1 to 1000 ppm in the liquid phase.

19. A method of epoxidizing a $C_2$–$C_{10}$ aliphatic olefin comprising reacting said $C_2$–$C_{10}$ aliphatic olefin with hydrogen peroxide at a temperature of 20° C. to 80° C. in a liquid phase within a reaction zone in the presence of a solvent, a titanium-containing molecular sieve catalyst, and a salt comprising an anionic species selected from the group consisting of halides, phosphates, sulfates, carbonates, carboxylates, hydroxide, alkoxides, and nitrate and a cation selected from ammonium, lithium, sodium, and potassium and a chelating agent having at least two functional groups, said functional groups being the same or different and selected from the group consisting of amino, hydroxy, carboxyl, phosphoryl and combinations thereof with at least two of said functional groups being carboxyl or phosphoryl, wherein the salt is present at a concentration of from 0.00001M to 0.02M in said liquid phase and the polyfunctional chelating agent is present at a concentration of from 1 to 1000 ppm in said liquid phase.

20. The method of claim 19 wherein the anionic species is hydroxide.

21. The method of claim 19 wherein the chelating agent is aminotrimethylene phosphonic acid.

22. The method of claim 19 wherein the $C_2$–$C_{10}$ aliphatic olefin is propylene.

\* \* \* \* \*